(12) United States Patent
Teplyashin

(10) Patent No.: US 7,915,039 B2
(45) Date of Patent: Mar. 29, 2011

(54) METHOD FOR OBTAINING MESENCHYMAL STEM CELLS

(76) Inventor: Alexander S. Teplyashin, Moskau (RU)

( * ) Notice: Subject to any disclaimer, the term of this patent is extended or adjusted under 35 U.S.C. 154(b) by 0 days.

(21) Appl. No.: 11/969,772

(22) Filed: Jan. 4, 2008

(65) Prior Publication Data

US 2008/0102506 A1  May 1, 2008

Related U.S. Application Data

(63) Continuation of application No. 11/099,176, filed on Apr. 4, 2005, now abandoned.

(30) Foreign Application Priority Data

Apr. 9, 2004 (RU) .............................. 2004110701

(51) Int. Cl.
*C12N 9/12* (2006.01)
(52) U.S. Cl. ..................... 435/325; 435/219; 435/183
(58) Field of Classification Search .................. None
See application file for complete search history.

(56) References Cited

U.S. PATENT DOCUMENTS 5,842,477 A * 12/1998 Naughton et al. ............ 128/898
2003/0161817 A1    8/2003 Young et al.
2003/0235563 A1   12/2003 Strom et al.

OTHER PUBLICATIONS

Campagnoli et al., Blood (2001) 98:2396-2402.
Fridenshtein et al., Exp. Hematol. (1974) 2:83-92.
Grontos et al., Blood (1995) 85:929-940.
Heynesworth et al., Bone (1995) 13:81-85.
Majumdar et al., J. Cell. Physiol. (2000) 185:98-106.
Rao et al., Mech. Ageing Dev. (2001) 122:713-734.
Romanov et at., Stem Cells. (2003) 21:105-110.
Zuk et al., Molecular Biology of the Cell (2002) 13:4279-4295.
Zuk et al. (2001) Multilineage Cells from Human Adipose Tissue: Implications for Cell-Based Therapies. Tissue Engineering 7(2):211-228.

* cited by examiner

*Primary Examiner* — Lisa J Hobbs
(74) *Attorney, Agent, or Firm* — Klarquist Sparkman, LLP

(57) ABSTRACT

The invention relates to the field of cell biology. In detail it relates to the obtainment of mesenchymal stem cells from human tissue. This invention might be applicable in healing within the frame of the treatment of several diseases.

Due to the invention it will be possible to obtain mesenchymal stem cells from human tissue with high homogeneity of the cell suspension, since the used method for obtaining mesenchymal stem cells from human tissue comprises the crushing and enzymatical treatment of the tissue with collagenase solution in Eagle medium in the Dulbecco modification, removal of erythrocytes by the aid of the lysis solution and subsequent filtration of the prepared suspension; as human tissue fat tissue or decidual or amniotic placenta membrane or chorion placenta stroma is used, whereas the filtration is performed sequentially by the use of filters comprising a pore size of 100 μm and 10 μm. In the enzymatical treatment of the fat tissue, of the decidual or amniotic placenta membrane collagenase of the type I is used, and in the enzymatical treatment of the chorion placenta stroma collagenase of the type IV is used.

19 Claims, No Drawings

METHOD FOR OBTAINING MESENCHYMAL STEM CELLS

CROSS REFERENCE TO RELATED APPLICATIONS

This application is a continuation of U.S. patent application Ser. No. 11/099,176, filed on Apr. 4, 2005 now abandoned, which claims priority to Russian Patent Application No. RU 2004110701 filed on Apr. 9, 2004, both of which are incorporated herein by reference.

BACKGROUND OF THE INVENTION

1. Field of the Invention

The invention relates to the field of cell biology. In detail it relates to the obtainment of mesenchymal stem cells from human tissue. This invention might be applicable in healing within the frame of the treatment of several diseases.

2. Related Prior Art

Currently in biomedical sciences a new field is developing: cell therapy. By means of cell transplantation insufficient activities of tissue functions can be redressed and affected organs can be regenerated. The function of renewal and restoration is taken over from stem cells in vivo which form an agglomeration of non-differentiated precursors of different cells types which are kept in reserve. As a result of this the use of stem cells is a promising field of cell therapy. In this connection of particular importance is the obtainment of stem cells from human tissue.

At present one has been succeeded in obtaining different types of stem cells from the adult human organism. In detail they concern hematopoietic (blood cell precursors), neuronal (precursors of nerve tissue cells), mesenchymal cells (cells which are capable to differentiate into cells of mesenchymal origin as well as into other embryonic layer cells) and other.

It is characteristic for mesenchymal stem cells that they can be obtained and cultivated comparatively easily; they are also capable to proliferate in vitro over prolonged periods of time. Furthermore, they excel in a broad spectrum of differentiation. In this connection the attention is especially directed to the obtainment of mesenchymal stem cells from the adult human organism. However, till this day there is no universal method for the obtainment of stem cells.

For the first time stem cells could be obtained from the spinal marrow due to their ability of adhering to the surface of culture dishes (Fridenshtein A. J., Deriglazova U. F., Kulagina N. N. et al. Precursors for fibroblasts in different populations of hematopoietic cells as detected by the in vitro colony assay method. Exp. Hematol. 1974 Vol. 2. P. 83-92).

The disadvantage of this method consists in the lacking homogeneity of the obtained cell population. Nevertheless the adhesion of mesenchymal stem cells to plastics has been established as starting basis for further improved methods for obtaining mesenchymal stem cells.

A method for obtaining mesenchymal stem cells is known that results from the cells' ability of adhering to the surface of culture dishes, whereby specific batches of the embryonic bovine serum are used. Thus it was managed to obtain cells with a high ability of adhesion, high rate of proliferation and long maintaining multipotency (Heynesworth S. E., Goshima J., Goldberg V. M., Calplan A. I. Characterization of cells with osteogenic potential from the human bone marrow//Bone. 1995. Vol. 13. P. 81-85.)

The disadvantage of this method consists in the fact that the analysis of the serum during the search for a batch that is suitable for the cultivation of cells plenty of time and work is required; furthermore the reproduction of results is not possible.

It is known to obtain mesenchymal stem cells by a method by means of which a selection for antibodies against Stro-1 (antigen with unknown function) is performed, Stro-1 is temporarily expressed on the surface of mesenchymal stem cells (Grontos S., Simmons P. J. The growth factors requirements of Stro-1 positive human stromal precursors under serum-deprived conditions in vitro//Blood. 1995. Vol. 85. P. 929-940).

This method concerns an extreme complex process that is very time consuming due to the preliminary antibody preparation.

A method for obtaining mesenchymal stem cells is known by means of which mononuclear cells are obtained by centrifugation in a Ficoll gradient, a selection for antibodies against the surface antigen CD105 which is expressed on the surface of mesenchymal stem cells, as well as by a cultivation of cells which adhere to plastics. The portion of $CD105^+$ cells amount to 2 to 3% of the mononuclear cells. As a result it was possible to obtain a cell population which shows the morphology and the expression profile of the surface antigens which are characteristic for mesenchymal stem cells and which also have chondregenic potential (Majumdar M. K., Banks V., Peluso D. P., Morris E. A. Isolation, characterization, and chondregenic potential of human bone marrow-derived multipotential stromal cells//J. Cell. Physiol. 2000. Vol. 185. P. 98-106).

This method enables the obtainment of the $CD105^+$ cell fraction which is enriched in mesenchymal stem cells; however, this method requires an additional selection stage in which antibodies immobilized to magnetic beads are used. Thereby a portion of cells gets lost so that additional efforts are required.

It is known that with increasing age the number of mesenchymal stem cells in the human organism is diminished conspicuously. This also apply to their ability to proliferate and differentiate (Rao M. S., Mattson M. P. Stem cell and aging: expanding the possibilities//Mech. Ageing Dev. 2001. Vol. 122. P. 713-734). For this reason one is working on the preparation of mesenchymal stem cells with high proliferative activity and potential for differentiation, which are for example originating from fetal tissue or larvae organs, respectively.

A method for obtaining mesenchymal stem cells from fetal progeny blood is known in the art. To obtain them the mononuclear cell fraction is prepared by centrifugation in the Ficoll gradient and they are cultivated under conditions which are beneficial for the growth of mesenchymal stem cells. The so obtained cells show osteogenetic or adipogenetic potential, respectively (Campagnoli C., Roberts I. A., Kumar S. et al. Identification of mesenchymal stem/progenitor cells in human first trimester fetal blood, liver, and bone marrow// Blood. 2001. Vol. 98. P. 2396-2402).

The disadvantage of the obtainment of mesenchymal stem cells from this source consists in the fact that fetal tissue is problematic in view of its accessibility. Moreover one has to face ethic problems which are associated with its use. Furthermore, it has turned out that the obtained cell populations are not homogeneous: 76% of the samples contained osteoclast-like cells; they expressed the characteristic antigens CD45, CD51/CD61, and were negative for CD64 (marker for macrophages), SH2 (marker for mesenchymal stem cells), CD31 (marker for endothelial cells). Only 26% of the samples were composed of cells which were similar to mesenchymal stem cells and expressed SH2, SH3, SH4, MAB1470, CD13, CD29, CD49e, CD54, CD90, ASMA, and were negative for CD31 and vWF (marker for endothelial cells).

Known is the method for obtaining mesenchymal stem cells from the subendothelial layer of the umbilical vein (Romanov Y. A., Svinitskaya V. A., Smirnov V. N. Searching for alternative sources of postnatal human mesenchymal stem cells; candiate MSC-like cells from umbilical cord//Stem Cells. 2003. Vol. 21. P. 105-110). For these purposes the umbilical vein was treated inside with a collagenase IV solution for a short time (for 15 minutes). The so obtained cells were cultivated in DMEM-LG supplemented with 10% FBS. In this manner a cell population with fibroblast-like morphology was obtained; it expressed a range of antigens which was similar to mesenchymal stem cells: $ICAM1^{+/-}$, $VCAM1^{+}$, $CD34^{-}$; $MySM^{-}$ (smooth muscle myosine); $CD31^{-}$, $vWF^{-}$ (marker for endothelial cells); $CD14^{-}$, $CD45^{-}$, $CD68^{-}$ (marker for monocytes/macrophages), however it did express smooth muscle fibre actin ASMA. The so obtained cell population showed osteogenetic or adipogenetic potential in vitro.

The disadvantage of this method consists in the heterogeneity of the obtained cell population: The primary culture contained endothelial and smooth muscle cells, whereby the endothelial cells have not proliferated under these conditions, whereas the myocytes portion was maintained during the cultivation.

A method for obtaining mesenchymal stem cells from human lipoaspirate is known in the art. In this method fat tissue reduced to small pieces is exposed to the effect of collagenase (type I). After neutralization of the collagenase and rinsing of the cell suspension a purification is performed in order to remove cell residues by the use of filters having a pore size of 100 μm. By doing so a population of mesenchymal stem cells could be obtained that showed a characteristic morphology, immunophenotype and that was able to differentiate into bone, cartilage, fat, muscle or nerve tissues, respectively (Zuk P. A., Zhu M., Ashjian P., De Ugarte D. D., Huang J. I., Mizuno H., Alfonso Z. C., Fraiser J. K. Benhaim P. and Hedrick M. H. Human adipose tissue is source of multipotent stem cells//Molecular Biology of the Cell. 2002. Vol. 13. P. 4279-4295).

This method has the disadvantage that the obtained cell suspension is heterogenous and the yield is low.

SUMMARY OF THE INVENTION

With the present invention it is now possible to obtain mesenchymal stem cells from human tissue, whereby the cell suspension has a high homogeneity.

Against this background, an object of the present invention is a method for obtaining and/or isolating mesenchymal stem cells from human tissue, comprising the following steps: (a) providing human tissue, (b) enzymatical and mechanical treatment of said human tissue for obtaining a cell suspension, (c) removal of erythrocytes from said suspension, and (d) filtration of said suspension for obtaining mesenchymal stem cells, wherein in step (a) fat tissue or/and placenta tissue is used as human tissue.

Within the frame of the method for obtaining mesenchymal stem cells from human tissue fat tissue or placenta is used as human tissue. This method might comprise the crushing and enzymatic treatment of the tissue with a solution of collagenase in Eagle medium in the Dulbecco modification, the removal of erythrocytes by the aid of lysing buffer solution and the subsequent filtration of the obtained suspension. The filtration can be performed sequentially by means of filters comprising a pore size of 100 μm and 10 μm. The filtration step can be performed by the use of a first filter comprising a pore size of 100 μm in diameter, and the subsequent use of a second filter comprising a pore size of 10 μm in diameter.

Collagenase type I can be used for the enzymatic treatment of the fat tissue, the decidual or amniotic membrane of the placenta. For the enzymatic treatment of the stroma of the chorionic placenta collagenase type IV is used.

The technical results of the invention (increase of the homogeneity of the cell suspension, increase of the yield of the target product and improved viability of the cells) attribute to the conditions for the filtration: Specific size of the filter pores and specific ratio of the pores of the used filters. The change (increase or decrease) of these parameters will have the result that the stated technical results will not be achieved, since in this case the yield of the target product and the homogeneity of the obtained cell suspension will be conspicuously reduced. In comparison to known similar methods a multiple yield of cells can be obtained. According to the applicant by performing the known methods the yield amounts to $10^4$ cells each tissue sample having a mass of 1 gram, whereas by performing the method according to the invention the yield of cells amounts to between 1.5 to $3 \times 10^4$ and $10^7$ cells each 1 gram of several tissue samples. The increase of the homogeneity of the cell suspension is proved by the data of the morphological analysis and the determination of the immunophenotype. According to the data of the applicant by using the known method by which the population of mesenchymal stem cells is obtained from lipoaspirate, the population contains multiple morphological cell types; not before the $4^{th}$ passage the culture becomes homogenic in view of their cell shape and granulation or the expression of surface markers, respectively.

The method is realized as follows:

First of all a tissue sample is rinsed with physiological saline solution with phosphate buffer (PBS) at pH 7.2 without $Ca^{2+}$ and $Mg^{2+}$ ions, supplemented with antibiotics (penicillin 100 units/ml, streptomycin 100 microgram/ml) and antimycotics (amphotericin B 0.25 microgram/ml). The tissue to be treated is reduced to small pieces; the eagle medium in the Dulbecco modification with above-mentioned antibiotics and antimycotics is added with a volume ratio between tissue and medium of 1:5 to 1:10 (DMEM, Dulbecco's Modified Eagle Medium). For the enzymatic treatment collagenase solution is added to the suspension until a final concentration of 0.075% is reached. The suspension is incubated for 30 minutes at 37° C., whereby the suspension is swung carefully.

The so prepared mixture is agitated until a homogenic suspension is produced; subsequently for neutralization of the collagenase an equivalent volume of the DMEM medium is added to the prepared mixture, which contains 10% by volume of fetal bovine serum (FBS). Afterwards a centrifugation at 1000 g for 10 minutes is performed. The pellet is resuspended in the erythrocyte lysis buffer solution (155 mM $NH_4Cl$, 10 mM $KHCO_3$, 0.1 mM $Na_2EDTA$). The mixture is thoroughly mixed and incubated for 3 to 5 minutes at room temperature.

The suspension is diluted with an equivalent volume of the DMEM medium that contains antibiotics and antimycotics; subsequently the cells are pelleted by centrifugation for 10 minutes at 1000 g. The pellet is rinsed with DMEM medium and again pelleted by centrifugation in the manner as described. The cells are brought into suspension in DMEM-LG medium with a concentration of glucose of 1 g/l, supplemented with 20% FBS, antibiotics and antimycotics. The so prepared cell suspension is filtered by the use of filters comprising a pore size of 100 μm and 10 μm, and 1 million cells each are plated per 1 $cm^2$.

The so obtained cell population is characterized by the high homogeneity of mesenchymal stem cells, whereby the alteration of the filtration data (increase and/or decrease of the pore size) results in a reduction of the homogeneity of the target product or the yield of cells, respectively.

DESCRIPTION OF PREFERRED EMBODIMENTS

The invention is illustrated by the following embodiments:

Example 1

The decidual membrane is separated from the placenta by means of small scissors. A tissue sample of 2 g is rinsed with PBS (Gibco) at pH 7.2 without $Ca^{2+}$ and $Mg^{2+}$ ions for three times, whereby the PBS contains a one-fold solution of antibiotics or antimycotics (Gibco), respectively, in which the final concentration of penicillin is 100 units/ml, streptomycin 100 microgram/ml, amphotericin B 0.25 microgram/ml.

The tissue is reduced to small pieces in a Petri dish by means of scissors; then the DMEM medium (Gibco) having a volume of 25 ml is added, which contains antibiotics and antimycotics; the tissue is resuspended and given into a 50 ml test tube (Costar).

To the so prepared suspension for the enzymatic treatment 1 ml of a solution containing 2% collagenase of type I (Gibco) is added until a final concentration of 0.075% is reached. The suspension is incubated for 30 minutes at 37° C. in a shaker, whereby slow swinging movements should be performed.

The mixture is thoroughly stirred until a homogenic suspension is produced; afterwards 25 ml DMEM medium is added to the mixture that contains 10% FBS (HyClone, PerBio) in order to neutralize the collagenase. The cells are pelleted by centrifugation for 10 minutes at 1000 g.

The supernatant is removed. In order to lyse the erythrocytes the pellet is resuspended in 20 ml of cold buffer solution which contains 155 mM $NH_4Cl$, 10 mM $KHCO_3$, 0.1 mM $Na_2EDTA$. The mixture is thoroughly stirred and incubated for 3 to 5 minutes at room temperature.

The so prepared suspension is diluted with DMEM medium that contains 25 ml antibiotics and antimycotics (Gibco); subsequently the cells are pelleted by centrifugation for 10 minutes at 1000 g.

The supernatant is removed. The cell supernatant is suspended in DMEM medium for washing. The cells are pelleted by centrifugation for 10 minutes at 1000 g.

The so prepared cell pellet is suspended in 25 ml DMEM-LG medium having a glucose concentration of 1 g/l (Gibco), supplemented with 20% FBS (HyClone, PerBio), one-fold solution of essential amino acids (Gibco) as well as a one-fold solution of antibiotics and antimycotics (100 units/ml penicillin, 100 microgram/ml streptomycin, 0.25 microgram/ml amphoterimycin B, Gibco).

The cell suspension is sequentially filtered by the use of filters comprising a pore size of 100 µm and 10 µm (Millipore) in order to remove cell residues and debris.

The number of purified cells is calculated in the Gorjajev chamber. The total cellular yield amounts to $10^8$/1 g of tissue. The cells are plated in 75 $cm^2$ flasks at 1 million/1 $cm^2$ each. The portion of adhering cells amounts to about 1%; the yield of mesenchymal stem cells from the decidual membrane amounts to approximately $10^6$/1 g of tissue.

After 24 hours the medium for the cells is replaced by fresh medium. Once the monolayer is reached the cells are sub-cultivated and visually evaluated in view of their morphology by the use of a phase contrast microscope; the mitosis index and the cellular generation time are calculated.

On account of the morphological analysis two major cell populations have been determined according to their phenotype. The first cell type presents itself as fusiform cells having a diameter of 15 to 35 µm with homogeneous cytoplasm, low nucleus-cytoplasm ratio, a centric nucleus consisting of 4 to 7 nucleoli. The second type comprises larger fibroblast-like, spread cells having a diameter of 90 µm with cytoplasm of diverse homogeneity; it has a low nucleus-cytoplasm ratio, a centric nucleus with 2 to 4 nucleoli. Thus, the cells to be analyzed have a morphology that is characteristic for human mesenchymal stem cells.

The mitosis index is calculated in the phase of logarithmic growth as the ratio of the number of mitosis to the total cell number. The mitosis index amounts to 29.5%. The cell generation time amounts to 29 hours.

The so obtained cells were immunophenotyped by staining with antibodies against the surface antigens CD10, CD13, CD31, CD34, CD44, CD45, CD90, CD105, CD117 (Becton Dickinson), whereby indirect fluorescence is used. The evaluation is performed by the use of a flowcytometer (Beckman Coulter). The surface marker expression corresponds to the immunophenotype of the mesenchymal stem cells: The cells are positive for CD13, CD44, CD90, CD105 and negative for CD31, CD34, CD45, CD117. The CD10 expression is moderately positive (table 1).

TABLE 1

Expression of the surface antigens on the surface of mesenchymal stem cells from the decidual placenta membrane. Immunophenotype of mesenchymal stem cells from the decidual membrane

| CD | % |
| --- | --- |
| CD10 | 50.30 |
| CD13 | 87.00 |
| CD31 | 1.50 |
| CD34 | 1.30 |
| CD44 | 95.90 |
| CD45 | 3.40 |
| CD90 | 93.70 |
| CD105 | 95.50 |
| CD117 | 7.00 |

Example 2

The chorion stroma is separated from the placenta by means of small scissors. The tissue sample of 5 g is rinsed three times with PBS (Gibco) at pH 7.2, without $Ca^{2+}$ and $Mg^{2+}$ ions. PBS (Gibco) contains a one-fold antibiotics and antimycotics solution (Gibco). The final concentration of penicillin is 100 units/ml, of streptomycin 100 microgram/ml, amphotericin B 0.25 microgram/ml.

The tissue is reduced to small pieces in 10 cm Petri dishes by means of scissors; subsequently 25 ml DMEM (Gibco) medium comprising antibiotics and antimycotics are added; afterwards, the tissue is suspended and given into a 50 ml test tube (Costar).

To the so prepared suspension for the enzymatic treatment 1 ml of a solution of 2% collagenase type IV (Gibco) is added until a final concentration of 0.075% is reached. The suspension is incubated for 30 minutes at 37° C. in a shaker with slow swinging movements.

The so prepared mixture is thoroughly stirred until a homogenic suspension is produced; afterwards 25 ml DMEM medium that contains 10% FBS (HyClone, PerBio) is added in order to neutralize the collagenase. The cells are pelleted by centrifugation for 10 minutes at 1000 g.

The supernatant is removed. For lyses of the erythrocytes the pellet is resuspended in 20 ml of cold buffer solution which contains 155 mM $NH_4Cl$, 10 mM $KHCO_3$, 0.1 mM $Na_2EDTA$. The mixture is thoroughly stirred and incubated for 3 to 5 minutes at room temperature.

The suspension is diluted with DMEM medium that contains antibiotics and antimycotics (Gibco) in a volume of 25 ml; afterwards the cells are pelleted by centrifugation for 10 minutes at 1000 g.

The supernatant is removed. In order to wash the cell residue the latter is suspended in DMEM medium. The cells are pelleted by centrifugation for 10 minutes at 1000 g.

The so prepared cell pellet is suspended in 25 ml DMEM-LG medium having a glucose concentration of 1 mg/ml (Gibco), supplemented with 20% FBS (HyClone, PerBio), a one-fold solution of essential amino acids (Gibco) and a one-fold solution of antibiotics and antimycotics (100 units/ml penicillin, 100 microgram/ml streptomycin, 0.25 microgram/ml amphoterimycin B, Gibco).

The cell suspension is sequentially filtered by the use of filters comprising a pore size of 100 μm and 10 μm (Millipore) in order to remove cell residues and debris.

The number of purified cells is calculated by evaluation in the Gorjajev chamber. The total yield of cells amounts to $10^9/1$ g of tissue. The cells are plated in 75 $cm^2$ flasks at 1 million/1 $cm^2$ each. The portion of the adhering cells amounts to about 1%; the yield of mesenchymal stem cells from the chorion stroma amounts to approximately $10^7/1$ g of tissue.

After 24 hours the medium for the cells is replaced by fresh medium. Once the monolayer is reached the cells are subcultivated, visually evaluated in view of the morphology by the use of a phase contrast microscope; the mitosis index and the cell generation time are calculated.

As a result of the morphological analysis two major cell populations were identified according to their phenotypes. The first cell type presents itself as fusiform cells having a diameter of 20 to 40 μm with homogenic cytoplasm, a low nucleus-cytoplasm ratio, a centric nucleus consisting of 4 to 7 nucleoli. The second type comprises larger fibroblast-like, spread cells having a diameter of 100 μm with cytoplasm of various homogeneity; it comprises a low nucleus-cytoplasm ratio, a centric nucleus with 2 to 4 nucleoli. Thus, the cells to be analyzed have a morphology that is characteristic for human mesenchymal stem cells.

The mitosis index is calculated in the phase of logarithmic growth as the ratio of the number of mitosis to the total cell number. The mitosis index amounts to 31.8%. The cell generation time amounts to 28 hours.

The so obtained cells are immunophenotyped by staining with antibodies against the surface antigens CD10, CD13, CD31, CD34, CD44, CD45, CD90, CD105, CD117 (Becton Dickinson), whereby indirect fluorescence is used. The evaluation is performed by the use of a cytometer (Beckman Coulter). The surface marker expression corresponds to the immunophenotype of the mesenchymal stem cells. The cells are positive for CD13, CD44, CD90, CD105 and negative for CD31, CD34, CD45, CD117. The CD10 expression is moderately positive (table 2).

TABLE 2

Expression of the surface antigens on the surface of mesenchymal stem cells from the chorion placenta stroma.
Immunophenotype of mesenchymal stem cells from the chorion stroma

| CD | % |
|---|---|
| CD10 | 84.40 |
| CD13 | 90.90 |
| CD31 | 0.20 |
| CD34 | 0.30 |
| CD44 | 97.60 |
| CD45 | 1.50 |
| CD90 | 95.30 |
| CD105 | 92.70 |
| CD117 | 3.90 |

Example 3

The amniotic membrane is separated from the placenta by means of small scissors. The tissue sample having a mass of 2 grams is rinsed three times in PBS (Gibco) at pH 7.2, without $Ca^{2+}$ and $Mg^{2+}$ ions. PBS (Gibco) contains a one-fold antibiotics or antimycotics solution (Gibco), respectively, the final concentration of penicillin is 100 units/ml, streptomycin 100 microgram/ml, amphotericin B 0.25 microgram/ml.

The tissue is reduced to small pieces in 10 cm Petri dishes by means of scissors; subsequently DMEM (Gibco) medium that contains antibiotics and antimycotics is added in a volume of 25 ml; the tissue is suspended and transferred in a 50 ml test tube (Costar).

For the enzymatic treatment to the so prepared suspension 1 ml of a solution of 1% collagenase of type I (Gibco) is added until a final concentration of 0.075% is reached. The suspension is incubated for 30 minutes at 37° C. in a shaker with slow swinging movements.

The so prepared mixture is thoroughly stirred until a homogeneous suspension is produced; then 25 ml DMEM medium that contains 10% FBS (HyClone, PerBio) is added in order to neutralize the collagenase. The cells are pelleted by centrifugation for 10 minutes by 1000 g.

The supernatant is removed. In order to lyse the erythrocytes the pellet is resuspended in 20 ml of cold buffer solution which contains 155 mM $NH_4Cl$, 10 mM $KHCO_3$, 0.1 mM $Na_2EDTA$. The mixture is thoroughly stirred and incubated for 4 minutes at room temperature.

The so prepared suspension is diluted with DMEM medium that contains antibiotics and antimycotics (Gibco) in a volume of 25 ml. Subsequently the cells are pelleted by centrifugation for 10 minutes at 1000 g.

The supernatant is removed. The cell pellet is suspended in DMEM medium for washing. The cells are pelleted by centrifugation for 10 minutes at 1000 g.

The so prepared cellular pellet is suspended in 25 ml DMEM-LG medium having a glucose content of 1 g/l (Gibco), supplemented with 20% FBS (HyClone PerBio), one-fold solution of essential amino acids (Gibco) as well as one-fold antibiotics and antimycotics solution (100 units/ml penicillin, 100 μg/ml streptomycin, 0.25 μg/ml amphotericin B (Gibco).

The cell suspension is sequentially filtered by the use of filters comprising a pore size of 100 μm and 10 μm (Millipore). The number of purified cells is evaluated by calculation in the Gorjajev chamber. The total yield of cells amounts to $10^8/1$ g of tissue. The cells are plated in 75 $cm^2$ flasks of 1 million/1 $cm^2$ each. The portion of the adhering cells amounts to about 1%; the yield of mesenchymal stem cells from the amniotic membrane amounts to approximately $10^6/1$ g of tissue.

After 24 hours the medium for the cells is replaced by fresh medium. Once the monolayer is reached the cells are sub-cultivated, visually evaluated in view of their morphology by the use of a phase contrast microscope; the mitosis index and the cell generation time are calculated.

As a result of the morphological analysis two major cell populations were determined. The first cell type presents itself as fusiform cells having a diameter of 10 to 30 µm with homogenous cytoplasm, low nucleus-cytoplasm relation, centric nucleus consisting of 4 to 7 nucleoli. The second type comprises larger fibroblast-like, spread cells having a diameter of 80 µm with cytoplasm of various homogeneity; it comprises a lower nucleus-cytoplasm relationship, a central nucleus consisting of 2 to 4 nucleoli. Thus, the cells to be analyzed show a morphology that is characteristic for human mesenchymal stem cells.

The mitosis index is calculated in the phase of logarithmic growth as the ratio of the number of mitosis to the total cell number. The mitosis index amounts to 31.6%. The cell generation time amounts to 25.7 hours.

The so obtained cells are immunophenotyped by staining with antibodies against the surface antigens CD10, CD13, CD31, CD34, CD44, CD45, CD90, CD105, CD117 (Beckton Dickinson), whereby indirect fluorescence is used. The evaluation is performed by use of a cytometer (Beckman Coulter). The surface marker expression corresponds to the immunophenotype of mesenchymal stem cells. The cells are positive for CD13, CD44, CD90, CD105, and negative for CD31, CD34, CD45, CD117. The CD10 expression is moderately positive (table 3).

TABLE 3

Expression of surface antigens at the surface of mesenchymal stem cells from the amniotic placenta membrane.
Immunophenotype of mesenchymal stem cells from the amniotic membrane

| CD | % |
| --- | --- |
| CD10 | 58.70 |
| CD13 | 93.20 |
| CD31 | 1.70 |
| CD34 | 1.40 |
| CD44 | 98.30 |
| CD45 | 0.00 |
| CD90 | 92.60 |
| CD105 | 96.90 |
| CD117 | 1.70 |

Example 4

A fat tissue sample having a mass of 10 g is rinsed three times in PBS (Gibco) at pH 7.2 without the ions $Ca^{2+}$ and $Mg^{2+}$. PBS (Gibco) contains a one-fold antibiotics and antimycotics solution (Gibco). The final concentration of penicillin is 100 units/ml, streptomycin 100 µg/ml, amphotericin B 0.25 µg/ml. The portions of compact connective tissue are removed.

Afterwards the tissue is subjected to mechanic fragmentation using medical scissors in 10 cm culture dishes (Costar), until a fine-dispersed mass is produced. It is transferred into two 50 ml test tubes having a cone-shaped bottom (Costar). Afterwards each sample is suspended in 25 ml DMEM medium that contains antibiotics and antimycotics.

Afterwards the enzymatic treatment is performed: to the so prepared suspension 1 ml of a solution of 2% collagenase of the type Gibco in the PBS buffer solution without Ca and $Mg^{2+}$ is added until a final enzyme concentration of 0.075% is reached. The suspension is incubated for 30 minutes at 37° C. at slow swinging movements.

The so prepared mixture is thoroughly mixed; then an equivalent DMEM volume is added that contains 10% FBS, antibiotics and antimycotics. The centrifugation lasts 10 minutes at 1000 g. The supernatant and the fat drops are removed. The pellets are pooled and suspended in 10 ml of cold lysine buffer solution (+4° C.) for 10 minutes, which contains 155 mM $NH_4Cl$, 10 mM $KHCO_3$, 0.1 mM $Na_2EDTA$. The mixture is thoroughly stirred and incubated for 3 to 5 minutes at room temperature.

Subsequently, 10 ml DMEM medium which contains antibiotics and antimycotics are added to the cell suspension. The cells are pelleted by centrifugation for 10 minutes at 1000 g.

The supernatant is removed and rinsed. The cell pellet is resuspended in 30 ml DMEM medium that contains antibiotics and antimycotics, and is centrifuged for 10 minutes at 1000 g.

The so obtained pellet is resuspended in 25 ml DMEM medium that contains antibiotics and antimycotics.

The so prepared cell suspension is filtered by the use of a filter comprising a pore size of 100 µm and is centrifuged for 10 minutes at 300 g. The pellet is resuspended in DMEM medium that is supplemented with antibiotics and antimycotics, 10% FBS and a one-fold solution of non-essential amino acids (Gibco) in a volume of 25 ml. The suspension is filtered by the use of a filter comprising a pore size of 10 µm.

In doing so, a homogenous cell fraction is produced that is free of cellular debris and blood cells.

The so prepared cell suspension is evaluated by calculation in the Gorjajev chamber and plated in 75 $cm^2$ flasks ($10^6$ cells/$cm^2$). The portion of adhering cells amounts to about 1% to 1.5%; the yield of mesenchymal stem cells which could be obtained from 1 g of fat tissue amounts to about $1.5-3\times10^4$ cells.

After 24 hours the medium is replaced by DMEM that contains antibiotics (100 units/ml penicillin, 100 µg/ml streptomycin (Gibco), 10% FBS and a one-fold solution of non-essential amino acids (Gibco).

Once the monolayer is reached, the cells are sub-cultivated, visually evaluated in view of the morphology by the use of a phase contrast microscope; the mitosis index and the cell generation time are calculated.

After the obtainment of cell fractions as a result of the morphological analysis two sub-populations were determined. The first cell type presents itself as a sub-population of fusiform cells having a diameter of 10 to 15 µm with exactly adjusted nucleus and homogenous cytoplasm. The second type is characterized by round cells with a flat cytoplasmatic outgrowth elongated on one side. The cell size amounts to 40 µm; a dark nucleus is observable which is displaced to the side, and a heterogenous cytoplasm. Also an increased granulation in the area of the nucleus is observable.

The mitosis index and the cell generation time is calculated in the phase of logarithmic growth. The ratio of the portion of cells being in mitosis to the total cell number amounts to 34%. The doubling time is about 54 to 62 hours.

The so obtained cells are immunophenotyped by the use of indirect fluorescence. By the use of a cytometer (Beckman Coulter) a high expression status of the following antigens could be determined: CD10 (CALLA), CD13 (APN), CD44 (hyaluronic acid receptor), CD90 (Thy-1), CD105 (endoglin) (Becton Dickinson). Furthermore, the lacking expression of the markers of hematopoietic cells—CD34, CD45 and CD117 (Becton Dickinson)—(table 4) was determined. The results of the determination of the immunophenotype prove that the population of the obtained cells corresponds to mesenchymal stem cells in view of their surface antigen expression.

TABLE 4

Surface antigen expression on the surface of
mesenchymal stem cells from fat tissue
Immunophenotype of mesenchymal stem cells from fat tissue

| CD | % |
|---|---|
| CD10 | 68.08 |
| CD13 | 96.53 |
| CD34 | 4.38 |
| CD44 | 93.08 |
| CD45 | 3.28 |
| CD90 | 98.36 |
| CD105 | 90.18 |
| CD117 | 2.30 |

The invention claimed is:

1. A method for obtaining and/or isolating mesenchymal stem cells from human tissue, comprising the following steps:
   (a) providing human tissue, wherein the human tissue is fat tissue, placenta tissue, or a combination thereof,
   (b) enzymatic and mechanical treatment of said human tissue to obtain a cell suspension,
   (c) removal of erythrocytes from said suspension, and
   (d) filtration of said suspension for obtaining mesenchymal stem cells,
   wherein in step (d) said suspension is firstly filtered through a first filter comprising a pore size of 100 μm, and secondly filtered through a second filter comprising a pore size of 10 μm, thereby obtaining and/or isolating mesenchymal stem cells.

2. The method according to claim 1, wherein in step (a) the human tissue is placenta tissue.

3. The method according to claim 1, wherein in step (a) the human tissue is fat tissue.

4. The method according to claim 1, wherein in step (b) for said enzymatic treatment collagenase is used.

5. The method according to claim 1, wherein in step (b) for said enzymatic treatment collagenase of type I is used.

6. The method according to claim 1, wherein in step (b) for said enzymatic treatment collagenase is used, wherein collagenase is provided in Dulbecco's modified Eagle medium.

7. The method according to claim 1, wherein in step (b) for said enzymatic treatment collagenase is used, wherein collagenase is provided in a final concentration of about 0.075%.

8. The method according to claim 1, wherein in step (c) said removal of erythrocytes is performed by the aid of buffer capable of lysing said erythrocytes.

9. A method for obtaining mesenchymal stem cells from human tissue, comprising
   crushing and enzymatically treating said human tissue with collagenase type I in Dulbecco's modified Eagle medium, wherein said human tissue is fat tissue, placenta tissue or a combination thereof;
   removing erythrocytes using a lysis solution to prepare a suspension; and
   filtering the suspension, wherein said filtration comprises filtering the suspension through a filter with a pore size of 100 μm and filtering the suspension through a filter with a pore size of 10 μm;
   thereby obtaining mesenchymal stem cells.

10. The method according to claim 9, wherein the human tissue is fat tissue or placenta tissue.

11. A method for obtaining and/or isolating mesenchymal stem cells from human tissue, comprising the following steps:
   (a) providing human tissue,
   (b) enzymatic and mechanical treatment of said human tissue for obtaining a cell suspension,
   (c) removing erythrocytes from said cell suspension, and
   (d) filtering said suspension to obtain purified cells,
   (e) cultivating the purified cells to obtain mesenchymal stem cells, wherein in step (a) fat tissue or/and placenta tissue is said human tissue, and wherein in step (d) said suspension is firstly filtered through a first filter comprising a pore size of 100 μm, and secondly filtered through a second filter comprising a pore size of 10 μm, thereby obtaining and/or isolating mesenchymal stem cells, and wherein said human tissue is fat tissue, placenta tissue or a combination thereof.

12. The method according to claim 11, wherein in step (a) said human tissue is fat tissue.

13. The method according to claim 11, wherein in step (a) said human tissue is placenta tissue.

14. The method according to claim 11, wherein in step (a) said human tissue is a combination of fat tissue and placenta tissue.

15. The method according to claim 11, wherein step (e) the cultivation is performed for 24 hours.

16. The method of claim 1, wherein the mesenchymal stem cells are negative for CD34 expression.

17. The method of claim 16, wherein the mesenchymal stem cells are negative for CD31, CD45, and CD117 expression.

18. The method of claim 1, wherein the mesenchymal stem cells are positive for CD10, CD13, CD44, CD90 and CD105 expression.

19. The method of claim 1, wherein between $1.5 \times 10^4$ and $10^7$ mesenchymal stem cells are obtained per gram of human tissue.

* * * * *